(12) United States Patent
Pynson

(10) Patent No.: US 8,535,332 B2
(45) Date of Patent: Sep. 17, 2013

(54) TWO STAGE PLUNGER FOR INTRAOCULAR LENS INJECTOR

(75) Inventor: Joel Pynson, Toulouse (FR)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 13/556,326

(22) Filed: Jul. 24, 2012

(65) Prior Publication Data

US 2012/0289970 A1    Nov. 15, 2012

Related U.S. Application Data

(63) Continuation of application No. 11/719,898, filed as application No. PCT/IB2004/004343 on Nov. 30, 2004, now Pat. No. 8,246,631.

(51) Int. Cl.
*A61F 9/007*    (2006.01)

(52) U.S. Cl.
USPC ............................ 606/107; 623/6.12

(58) Field of Classification Search
USPC .................. 606/107, 166; 623/6.11, 6.12
See application file for complete search history.

(56) References Cited

U.S. PATENT DOCUMENTS

| | | |
|---|---|---|
| 4,126,345 A | 11/1978 | List |
| 4,681,102 A | 7/1987 | Bartell |
| 4,705,041 A | 11/1987 | Kim |
| 4,715,373 A | 12/1987 | Mazzocco et al. |
| 4,773,415 A | 9/1988 | Tan |
| 4,834,094 A | 5/1989 | Patton |
| 4,862,885 A | 9/1989 | Cumming |
| 4,900,300 A | 2/1990 | Lee |
| 4,919,130 A | 4/1990 | Stoy et al. |
| 4,986,586 A | 1/1991 | Eilrich et al. |
| 5,197,815 A | 3/1993 | Sibley |
| 5,441,496 A | 8/1995 | Easley et al. |
| 5,599,330 A | 2/1997 | Rainin |
| 5,603,698 A | 2/1997 | Roberts et al. |

(Continued)

FOREIGN PATENT DOCUMENTS

| | | |
|---|---|---|
| CN | 2291910 | 9/1998 |
| EP | 1360946 | 11/2003 |

(Continued)

OTHER PUBLICATIONS

English Translation of Office Action in corresponding Chinese application (CN00480044520.3) dated Mar. 10, 2009.

(Continued)

*Primary Examiner* — Ryan Severson
*Assistant Examiner* — Rachel S Papeika
(74) *Attorney, Agent, or Firm* — Jeffrey B. Powers

(57) ABSTRACT

A plunger for an IOL injector device includes a shaft with a distal tip and a compressible sleeve positioned about the shaft with the tip extending forwardly of the sleeve. In a first stage of IOL advancement through the injector device, the plunger tip engages and pushes the IOL through a first section of the injector body. In a second stage of IOL advancement, the sleeve enters the narrowing section of the injector body toward the open tip thereof with the IOL and sleeve both undergoing compression. The sleeve compresses and lengthens in a forward direction ultimately enveloping the plunger distal tip. Viscoelastic applied inside the injector accumulates between the leading edge of the compressed sleeve and the compressed IOL thereby creating hydraulic pressure which pushes the compressed IOL through the remainder of the injector body and out the open distal tip thereof.

2 Claims, 2 Drawing Sheets

(56) References Cited

U.S. PATENT DOCUMENTS

| | | |
|---|---|---|
| 5,603,710 A | 2/1997 | Easley et al. |
| 5,718,677 A | 2/1998 | Capetan et al. |
| 5,735,858 A | 4/1998 | Makker et al. |
| 5,772,666 A | 6/1998 | Feingold et al. |
| 5,776,138 A | 7/1998 | Vidal et al. |
| 5,807,400 A | 9/1998 | Chambers et al. |
| 5,830,192 A | 11/1998 | Van Voorhis |
| 5,868,752 A | 2/1999 | Makker et al. |
| 5,873,851 A | 2/1999 | Nilsson |
| 5,876,407 A | 3/1999 | Makker et al. |
| 5,935,096 A | 8/1999 | Barrett |
| 5,944,725 A | 8/1999 | Cicenas et al. |
| 5,947,976 A | 9/1999 | Van Noy et al. |
| 5,976,150 A | 11/1999 | Copeland |
| 5,997,562 A | 12/1999 | Zadno-Azizi et al. |
| 6,010,510 A | 1/2000 | Brown et al. |
| 6,015,403 A | 1/2000 | Jones |
| 6,022,358 A | 2/2000 | Wolf et al. |
| 6,056,758 A | 5/2000 | Vidal et al. |
| 6,083,231 A | 7/2000 | Van Noy et al. |
| 6,129,733 A | 10/2000 | Brady et al. |
| 6,143,001 A | 11/2000 | Brown et al. |
| 6,156,054 A | 12/2000 | Zadno-Azizi et al. |
| 6,162,229 A | 12/2000 | Feingold et al. |
| 6,254,607 B1 | 7/2001 | Makker et al. |
| 6,290,690 B1 | 9/2001 | Huculak et al. |
| 6,334,862 B1 | 1/2002 | Vidal et al. |
| 6,336,932 B1 | 1/2002 | Figueroa et al. |
| 6,398,789 B1 | 6/2002 | Capetan |
| 6,447,519 B1 | 9/2002 | Brady et al. |
| 6,478,776 B1 | 11/2002 | Rosenman et al. |
| 6,500,181 B1 | 12/2002 | Portney |
| 6,537,283 B2 | 3/2003 | Van Noy |
| 6,558,395 B2 | 5/2003 | Hjertman et al. |
| 6,605,093 B1 | 8/2003 | Blake |
| 6,626,979 B2 | 9/2003 | Marsden et al. |
| 6,648,851 B2 | 11/2003 | Pyret et al. |
| 6,685,740 B2 | 2/2004 | Figueroa |
| 6,723,104 B2 | 4/2004 | Ott |
| 6,800,076 B2 | 10/2004 | Humayun |
| 6,866,655 B2 | 3/2005 | Hackett |
| 6,902,558 B2 | 6/2005 | Laks |
| 6,923,815 B2 | 8/2005 | Brady et al. |
| 6,976,989 B1 | 12/2005 | Vincent |
| 7,037,328 B2 | 5/2006 | Vincent |
| 7,094,243 B2 | 8/2006 | Mulholland et al. |
| 7,131,976 B2 | 11/2006 | Kobayashi et al. |
| 7,156,854 B2 | 1/2007 | Brown et al. |
| 7,189,245 B2 | 3/2007 | Kaplan |
| 7,204,820 B2 | 4/2007 | Akahoshi |
| 7,494,478 B2 | 2/2009 | Itou et al. |
| 7,537,593 B2 | 5/2009 | Humayun |
| 7,638,087 B2 | 12/2009 | Landuyt |
| 7,837,692 B2 | 11/2010 | Mulholland et al. |
| 7,947,049 B2 | 5/2011 | Vaquero |
| 8,177,777 B2 | 5/2012 | Humayun |
| 2002/0010476 A1 | 1/2002 | Mulholland et al. |
| 2003/0065345 A1 | 4/2003 | Weadock |
| 2004/0059343 A1 | 3/2004 | Shearer et al. |
| 2005/0171555 A1 | 8/2005 | Tran et al. |

FOREIGN PATENT DOCUMENTS

| | | |
|---|---|---|
| EP | 1415619 | 5/2004 |
| JP | 2001-008954 | 1/2001 |
| WO | WO96/37152 | 11/1996 |
| WO | WO97/15253 | 5/1997 |
| WO | WO98/37830 | 9/1998 |
| WO | WO2005/030097 | 4/2005 |
| WO | WO2007/005692 | 1/2007 |

OTHER PUBLICATIONS

English Translation of Office Action in corresponding Japanese application (JP 2007 543940) dated Oct. 27, 2009.

English Translation of Office Action in corresponding Japanese application (JP 2007 543940) dated Aug. 31, 2010.

English Translation of Office Action in corresponding Japanese application (JP 2007 543940) dated May 31, 2011.

TWO STAGE PLUNGER FOR INTRAOCULAR LENS INJECTOR

BACKGROUND OF THE INVENTION

This application is a continuation of application Ser. No. 11/719,898, filed Apr. 1, 2009, which claims the benefit of PCT/IB2004/004343, filed Nov. 30, 2004, which are incorporated by reference herein.

The present invention relates to ophthalmic surgical devices and methods. More particularly, the present invention relates to a novel plunger device and method for inserting an intraocular lens (hereinafter "IOL") into an eye.

IOLs are artificial lenses used to replace the natural crystalline lens of the eye when the natural lens has cataracts or is otherwise diseased. IOLs are also sometimes implanted into an eye to correct refractive errors of the eye in which case the natural lens may remain in the eye together with the implanted IOL. The IOL may be placed in either the posterior chamber or anterior chamber of the eye. IOLs come in a variety of configurations and materials. Some common IOL styles include the so-called open-looped haptics which include the three-piece type having an optic and two haptics attached to and extending from the optic; the one-piece type wherein the optic and haptics are integrally formed (e.g., by machining the optic and haptics together from a single block of material); and also the closed looped haptic IOLs. Yet a further style of IOL is called the plate haptic type wherein the haptics are configured as a flat plate extending from opposite sides of the optic. The IOL may be made from a variety of materials or combination of materials such as PMMA, silicone, hydrogels and silicone hydrogels, etc.

Various instruments and methods for implanting the IOL in the eye are known. In one method, the surgeon simply uses surgical forceps having opposing blades which are used to grasp the IOL and insert it through the incision into the eye. While this method is still practiced today, more and more surgeons are using more sophisticated IOL injector devices which offer advantages such as affording the surgeon more control when inserting the IOL into the eye. IOL injector devices have recently been developed with reduced diameter insertion tips which allow for a much smaller incision to be made in the cornea than is possible using forceps alone. Smaller incision sizes (e.g., less than about 3 mm) are preferred over larger incisions (e.g., about 3.2 to 5+mm) since smaller incisions have been attributed to reduced post-surgical healing time and complications such as induced astigmatism.

Since IOLs are very small and delicate articles of manufacture, great care must be taken in their handling. In order for the IOL to fit through the smaller incisions, they need to be folded and/or compressed prior to entering the eye wherein they will assume their original unfolded/uncompressed shape. The IOL injector device must therefore be designed in such a way as to permit the easy passage of the compressed IOL through the device and into the eye, yet at the same time not damage the delicate IOL in any way. Should the IOL be damaged during delivery into the eye, the surgeon will most likely need to extract the damaged IOL from the eye and replace it with a new IOL, a highly undesirable surgical outcome.

IOL injector devices typically incorporate a plunger that telescopes within a tubular injector body. As the plunger is advanced within the injector body, the distal plunger tip pushes the IOL through the injector body with the IOL ultimately exiting the device at the narrow open tip of the injector device. The surgeon positions the narrow open tip into the incision made in the eye to express the IOL from the injector open tip into the eye. The plunger tip is therefore a critical design component of the injector device in that it creates the force necessary to advance the IOL through the injector device. In most, if not all, of the injector devices on the market today, the injector tip makes direct contact with the IOL. It will be appreciated that direct contact of the IOL with any injector components increases the risk of damage to the IOL. Damage to IOL during delivery is many times attributable to the plunger tip which may inadvertently scratch or tear the IOL as it engages and advances the IOL through the injector device. The chance of IOL damage is heightened during the latter part of the IOL advancement stage where it is being compressed and pushed through the narrowing inserter passage at the same time. This is because the force required to push the IOL through the inserter device necessarily increases as the IOL is being compressed through the ever-narrowing injector lumen. This latter stage of IOL advancement is therefore a critical stage where forces upon the IOL are at their greatest and the IOL is more susceptible to damage caused by those forces.

There therefore remains a need for an injector device which will advance and expel the IOL from the injector open tip and into the eye in a non-destructive and controlled manner.

SUMMARY OF THE INVENTION

The present invention provides an improved plunger device and method for inserting an IOL into an eye. In a first aspect of the invention, the plunger of the present invention includes a rigid shaft having a distal tip and a compressible sleeve positioned about the rigid shaft with the distal tip extending forwardly of the uncompressed sleeve. In a first stage of IOL advancement, the plunger distal tip safely engages an IOL positioned within the injector body and advances the IOL for a first distance within the injector body. Preferably, this first distance imparts no or only small compressive forces to the IOL or sleeve. In a second stage of IOL advancement, the compressible sleeve begins compressing about the plunger shaft due to the narrowing walls of the injector body extending toward the open tip thereof. The sleeve compresses and thereby lengthens in a direction toward the distal tip of the plunger shaft. In a preferred embodiment of the invention, the sleeve deforms forwardly and ultimately completely envelops the distal tip of the plunger shaft. Lengthening of the sleeve in a rearward direction is preferably inhibited by a stop feature incorporated into the plunger and/or injector body. The optional but preferred presence of visco-elastic in the injector body is previously applied by the surgeon in an amount sufficient to create hydraulic pressure between the leading edge of the compressed sleeve and the IOL such that the IOL is advanced without direct contact of the optic with the compressed sleeve. As such, the chance of damage to the IOL is reduced, particularly during the critical stage of the IOL being compressed to its smallest diameter.

DETAILED DESCRIPTION

Figure 1A:
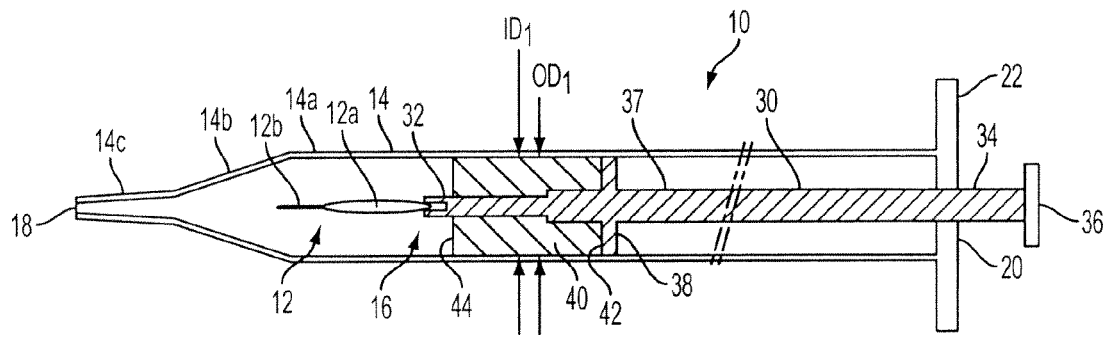
FIGS. 1a, b and c are cross-sectional views of a first embodiment of the invention showing successive stages of plunger and IOL advancement (1b and c being fragmented)

Referring now to the drawing, there is seen in the various Figures an IOL injector device designated generally by the reference numeral 10. Injector device 10 is used to deliver an IOL 12 into an eye (not shown). The configuration of injector device 10 shown in the Figures is for purposes of description only, it being understood that the injector device 10 may be of any desired configuration such as those employing separate IOL cartridges and/or nozzle tips which are joined to the injector body at the time of surgery (see, for example, U.S. Pat. No. 4,681,102). Still other injector body types may be seen in commonly assigned U.S. Pat. Nos. 5,944,725 and 6,336,932, for example. Injector 10 may furthermore be of the so-called "fully preloaded" or "partially pre-loaded" type wherein the IOL 12 is shipped loaded within the injector device 10, or in a component which is operable to transfer the IOL to the injector device without requiring direct handling of the IOL, respectively (see, e.g., commonly assigned U.S. application Ser. No. 10/813,863 and PCT application number PCT/03/04686). Likewise, the configuration of IOL 12 is also for purposes of description only, it being understood that the IOL configuration and material may be of any desired shape and type, the only requirement being that it be foldable or otherwise compressible to fit through a small ocular incision. In the Figures, IOL 12 is of the looped haptic type having an optic 12a with first and second haptics 12b, 12c extending from the optic periphery.

Injector device 10 is thus seen in FIG. 1a to include a tubular body 14 having a longitudinal opening 16 extending between an open distal tip 18 and open proximal end 20. Body 14 includes a main section 14a of substantially constant diameter which leads into a tapered section 14b which in turn leads into a distal section 14c terminating at open tip 18. As mentioned above, the configuration of the body 14 may vary from that described and shown herein including, but not limited to, the lengths and sizes of the section diameters leading to the open tip at which the IOL is expressed from the device 10. The diameter of the open tip 18 is preferably, although not necessarily, in the sub-3 mm range.

A finger ledge 22 is located adjacent body proximal end 20 to assist in manually operating device 10 in the manner of a syringe. In this regard, a plunger 30 is provided which telescopes through longitudinal opening 16 in body 14. Plunger 30 has an elongated, rigid shaft 37 with opposite distal and proximal ends 32, 34, respectively. A thumb press 36 is located adjacent proximal end 34 which is used in conjunction with finger ledge 22 to advance plunger 30 toward the distal open tip 18 of body 14 during operation of device 10. It is understood that the plunger may have any type of advancement mechanism, including, but not limited to, the so-called "screw-type" plunger where the plunger is threaded into the body and is advanced by the surgeon rotating the plunger proximal end.

Figure 2A:
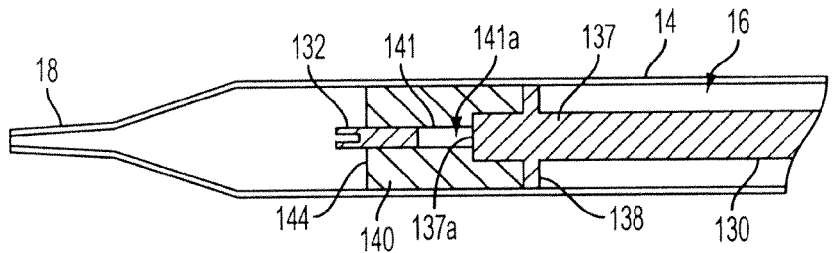
FIGS. 2a and b are fragmented, cross-sectional views of a second embodiment of the invention in successive stages of plunger advancement.
Figure 3A:
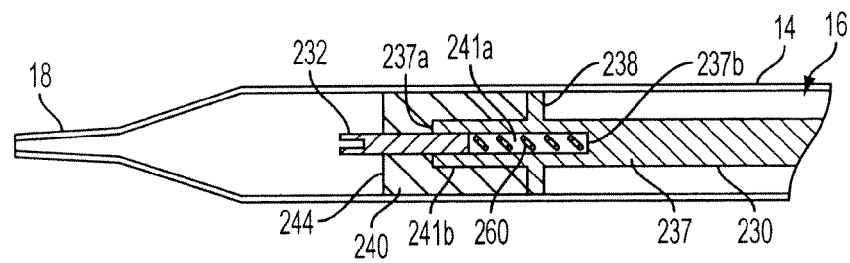
FIGS. 3a and b are fragmented, cross-sectional views of a third embodiment of the invention in successive stages of plunger advancement.

In one aspect of the invention, a compressible sleeve 40 is provided on plunger shaft 37 adjacent distal tip 32 with distal tip 32 spaced and uncovered by the sleeve 40 (see FIGS. 1a, 2a and 3a). Sleeve 40 is made from any suitable compressible material such as a silicone elastomer, for example. The outer diameter $OD_1$ of the uncompressed sleeve 40 is about equal to or slightly larger than the inner diameter $ID_1$ of longitudinal opening 16 whereby sleeve 40, even when under compression, may slide together with plunger shaft 37 inside longitudinal opening 16. A flange 38 is provided on plunger shaft 37 rearwardly of distal tip 32. Flange 38 has an outer diameter that preferably is only slightly smaller than the inner diameter $ID_1$ of longitudinal opening 16 such that flange 38 is freely slidable together with shaft 37 therein. The proximal end 42 of sleeve 40 abuts flange 38 which acts as a stop to prevent sleeve 40 from slipping or lengthening on shaft 37 in a rearward direction toward proximal end 34. In this regard, it is noted that sleeve 40 may be loosely fitted to shaft 37. Alternatively, at least a portion of the core of sleeve 40 may be fixed to shaft 37 by any desired means, e.g., adhesively, thermally, chemically, overmoulding, etc. In this situation it is possible, therefore, that instead of flange 38 being directly connected to or integral with shaft 37, flange 38 is fixed to sleeve end 42. With the sleeve 40 fixed to shaft 37 as described above, a flange 38 attached to sleeve proximal end 42 would still act to prevent rearward sliding or compressive movement of sleeve 40 on shaft 37. The term "sliding movement" means the entire sleeve 40 is sliding on shaft 37 whereas the term "compressive movement" means the sleeve core remains stationary on shaft 37 but the outer parts of the sleeve lengthen (and hence moves in a longitudinal direction on shaft 37) as a result of being compressed to a smaller diameter.

At the time of surgery, the device 10 is readied with IOL 12 properly located therein and the plunger 30 in its retracted position. The initial location and orientation of IOL 12 may of course vary according to the configuration of the device body 14 being used as described above. When the plunger 30 is in its initial retracted position, the distal tip 32 thereof is spaced rearwardly of IOL 12. To express IOL 12 from device 10, the surgeon presses upon thumb press 36 which causes the plunger shaft distal tip 32 to approach and then engage IOL optic 12a at the periphery thereof (see FIG. 1a). In this regard, it is noted the plunger distal tip 32 may be of any desired configuration, a bifurcated tip being shown in the Figures where the optic periphery becomes located between the prongs of the bifurcated tip (see FIG. 1a). The trailing haptic 12c becomes located rearwardly of the plunger tip so that it does not become entangled or otherwise damaged by the advancing plunger. In this regard, plunger 30 may incorporate a haptic relief (not shown) adjacent distal tip 32 thereof. Such a haptic relief is taught, for example, in commonly assigned copending application Ser. No. 10/813,862. In the case of an IOL having plate haptics, the plunger distal tip may engage the outer edge of the trailing haptic as seen commonly assigned U.S. Pat. No. 6,336,932.

Figure 1B:
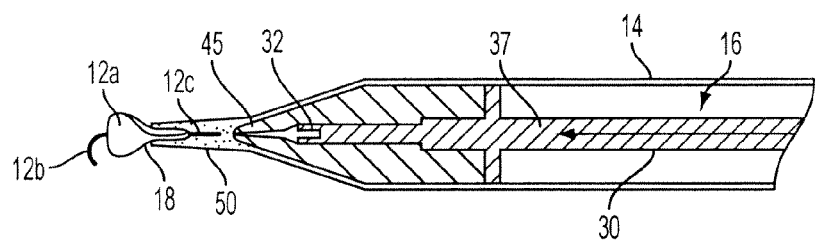

Upon continued pressing of thumb press 36, plunger distal tip 32 pushes the IOL 12 toward device open tip 18 with IOL 12 compressing as it travels through the narrowing body sections 14b and 14c. As sleeve 40 enters tapered section 14b, it undergoes successive compression by the gradual narrowing of the inner diameter of the longitudinal opening 16 along tapered body section 14b (see FIGS. 1b, 2b and 3b). As sleeve 40 compresses, it simultaneously deforms in a forward (distal) direction, lengthening in the process. As explained above, rearward movement of sleeve 40 with respect to shaft 37 is prevented by flange 38. As seen in FIG. 1b, this forward compressive movement of sleeve 40 eventually at least partially envelops the plunger shaft distal tip 32. In the preferred embodiment, the sleeve completely envelops tip 32 and extends forwardly thereof for a distance of between about 1 mm to about 15 mm, and more preferably between about 3 mm and 10 mm, and most preferably about 8 mm.

Figure 1C:
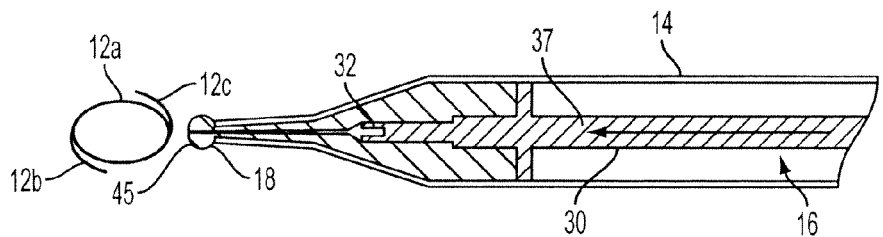

As is well known by those skilled in the art, a surgeon will typically apply a quantity of visco-elastic into the injector body 14 prior to advancing the IOL therethrough. As seen in FIG. 1b, the visco-elastic 50 is applied and becomes concentrated between the IOL 12 and the compressed sleeve leading edge 45. Since the area is effectively sealed between IOL 12 and compressed sleeve leading edge 45 at this point in the plunger advancement, the visco-elastic 50 creates hydraulic pressure which continues the push against IOL 12. Thus, as the surgeon continues to press upon thumb press 36, the visco-elastic 50 will push IOL 12 forwardly toward open tip 18. Seeing that the leading edge of the sleeve is soft, there is less likely damage to the IOL than if the IOL were contacted by the plunger distal tip through the second stage of IOL advancement (i.e., when the IOL is undergoing compression). As seen in FIGS. 1*b* and 1*c*, upon continued pressing of thumb press 36, the IOL 12 is eventually expressed out of open tip 18 whereupon it resumes its original shape.

Figure 2B:
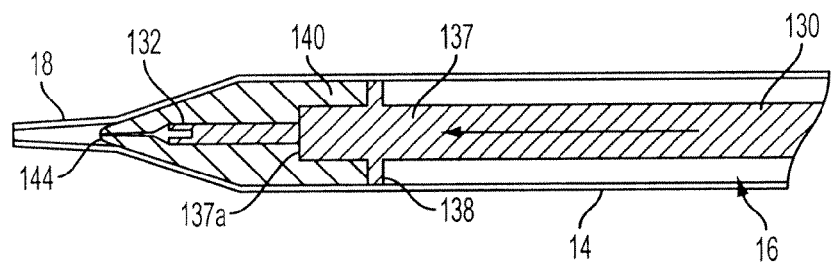

In an alternate embodiment of the invention seen in FIGS. 2*a* and 2*b*, distal tip 132 is separate from the remaining plunger shaft 137. Prior to plunger advancement, distal tip 132 is located within the forward part of sleeve core 141 with the tip extending outwardly therefrom as seen in FIG. 2*a*. The shaft distal portion 137*a* is located within the proximal portion of sleeve core 141 and, together with tip 132, define a space 141*a* therebetween. Distal tip 132 is loosely inserted into sleeve 140 such that tip 132 will be pushed rearwardly into space 141*a* upon advancement of plunger 130 and compression of sleeve 140. This embodiment therefore ensures the tip 132 will eventually become completely enveloped by sleeve 140 as seen in FIG. 2*b*. The compression of sleeve 140 and advancement of IOL 12 through and out device 10 otherwise proceeds in the same manner as in the embodiment of FIGS. 1*a-c* as described above.

Figure 3B:
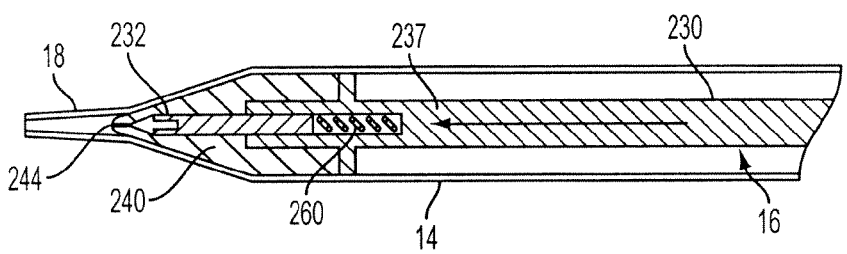

In still a further embodiment seen in FIGS. 3*a* and 3*b*, the plunger tip 232 is separate from the remainder of shaft 237 as in the embodiment of FIGS. 2*a* and 2*b*. However, in this embodiment, a bore 241*b* is formed in the shaft distal end 237*a* and plunger tip 232 is inserted into bore 241*b*. A space 241*a* is formed between the proximal end of the plunger tip 232 and the proximal end 237*b* of bore 241*b* wherein a spring 260 may be positioned. As the tip 232 is forced rearwardly into bore 241*b* upon advancement of plunger 230 and compression of sleeve 240, spring 260 compresses and provides a biasing force which may be used to more precisely control the movement of the tip 232 with respect to the shaft 237 and sleeve 240. The compression of sleeve 240 and advancement of IOL 12 through and out device 10 otherwise proceeds in the same manner as in the embodiment of FIGS. 1*a-c* as described above.

What is claimed is:

1. A method of preparing a device for surgery, said method comprising the steps of:
    a) providing a device body having a proximal end and a distal open tip and a longitudinal opening extending therebetween, said longitudinal opening having a narrowing section adjacent said distal open tip of said body;
    b) providing an IOL in said longitudinal opening;
    c) providing a plunger for sliding movement through first and second stages of advancement in said longitudinal opening, said second stage of advancement occurring within at least a portion of said narrowing section of said longitudinal opening, said plunger comprising:
        i) a rigid shaft having a proximal end and a distal tip; and
        ii) a compressible sleeve placed on said shaft adjacent said distal tip thereof, said distal tip extending forwardly of and uncovered by said sleeve when in the uncompressed condition,
    whereby said plunger may be advanced in said longitudinal opening through said first stage of advancement with said shaft distal tip engaging and pushing said IOL through said first stage of advancement, and whereby said plunger may be further advanced through said second stage of advancement with said sleeve undergoing compression and lengthening in a forward direction and thereby at least partially enveloping said shaft distal tip.

2. The method of claim 1, and further comprising the step of applying a viscoelastic between said plunger distal tip and said IOL in a quantity sufficient to create hydraulic pressure between said sleeve and said IOL during said second advancement stage.

\* \* \* \* \*